United States Patent [19]

Hirono et al.

[11] Patent Number: 5,610,672
[45] Date of Patent: Mar. 11, 1997

[54] OPHTHALMIC MEASUREMENT APPARATUS FOR MEASURING BIOLOGICAL PROPERTIES IN THE EYE

[75] Inventors: Taisuke Hirono; Kenkichi Ueda, both of Chofu, Japan

[73] Assignee: Kowa Company Ltd., Japan

[21] Appl. No.: 355,515

[22] Filed: Dec. 14, 1994

[30] Foreign Application Priority Data

Dec. 24, 1993 [JP] Japan ................................. 5-326490

[51] Int. Cl.⁶ ............................................ A61B 3/10
[52] U.S. Cl. .................................... 351/205; 351/208
[58] Field of Search ................................. 351/208, 221, 351/211, 205

[56] References Cited

U.S. PATENT DOCUMENTS 5,202,709  4/1993  Ichihashi et al. ..................... 351/221

Primary Examiner—William L. Sikes
Assistant Examiner—James A. Dudek
Attorney, Agent, or Firm—Adams & Wilks

[57] ABSTRACT

An ophthalmic measurement apparatus for measuring biological properties by scanning the anterior chamber of an eye two-dimensionally with a laser beam. Light received from the anterior chamber is measured at a plurality of measurement points in a target measurement range defined by the two-dimensional scanning. A representative background value at each of the measurement points is calculated from the received light and compared with a reference value to provide an alignment rank level indicative of the state of alignment. The state of alignment is determined according to the alignment rank level. A difference value between the representative background values or a standard deviation at the measuring points is calculated and compared with an associated reference value for improving the determination of the state of alignment.

33 Claims, 8 Drawing Sheets

VERTICAL SCANNING

HORIZONTAL SCANNING

OPHTHALMIC MEASUREMENT APPARATUS FOR MEASURING BIOLOGICAL PROPERTIES IN THE EYE

BACKGROUND OF THE INVENTION

2. Field of the Invention

The present invention relates to an ophthalmic measurement apparatus, and more particularly to an ophthalmic measurement apparatus which measures biological properties (for example, blood cells, cell parts detached from tissues, pigment cells, lipid, protein, floating cells, etc.) by spatially scanning the anterior chamber of an examinee's eye with a laser beam and receiving light scattered by biological particles in the anterior chamber and which can also determine the state of alignment of the apparatus with the eye.

2. Prior Art

A flare meter is conventionally known as an ophthalmic measurement apparatus which performs measurements after first determining the state of optical alignment by irradiating the anterior chamber of the eye and receiving light scattered and reflected therefrom.

A flare meter is used to measure the protein concentration (flare concentration) in the anterior chamber. Based on the assumption that the flare concentration in the anterior chamber is uniform, it is only necessary to measure the protein concentration at one point. To align the system prior to measurement, therefore, it is only necessary to know the state of alignment spatially in one dimension.

However, two-dimensional laser beam sweeping is required to measure indicators of biological properties formed by physical quantities having a spatial distribution, such as the density of floating particles in the anterior chamber or the protein concentration. It therefore follows that it is also necessary to sweep the laser beam two-dimensionally for alignment purposes.

Conventional ophthalmic measurement apparatuses are aligned in such a way that they work as a means for obtaining one-dimensional alignment information and an alignment determination function for selecting the optimum position for measurement.

As an example, a method of alignment used for a non-contact tonometer provides the optimum position for correctly measuring the intraocular pressure by bringing the corneal axis connecting the center of corneal curvature with the corneal apex into alignment with the optical axis of the optical observation system, and adjusting the distance between the center of corneal curvature and the tip of the nozzle.

On the other hand, alignment with a refractometer obtains the optimum position for measuring refractivity by using two reference beams to form an image at one point on the retina.

However, the above types of alignment arrangements are not suitable for use in locating an optimum place to measure physical quantities indicative of biological properties having a spatial distribution such as the density of floating particles in the anterior chamber or the protein concentration, thus resulting in a reduction of the 5 measurable range (what is determined as being measurable). The fact that the measurable range is thus severely restricted means that the alignment takes much time. Moreover, the condition of the patient's eye may further restrict good alignment locations, so that even more time is required for alignment. The result is that more time is needed for measurement, subjecting both the examiner and the examinee to physical and mental stress and discomfort.

An object of the present invention is to provide an ophthalmological apparatus being capable of determining system alignment to expand the measurable region, reduce measurement time and improve measurement accuracy in measuring biological properties by spatially scanning the anterior chamber of an examinee's eye with a laser beam and receiving light scattered by biological particles in the anterior chamber.

SUMMARY OF THE INVENTION

The invention achieves this object by providing an ophthalmic measurement apparatus which measures biological properties by spatially scanning the anterior chamber of an eye with a laser beam and receiving light scattered by biological particles in the anterior chamber and which can also determine the state of alignment of the apparatus with the eye, comprising: means for spatially scanning the anterior chamber of an eye with a laser beam; means for receiving reflected, scattered or disturbing light coming from the anterior chamber scanned by the laser beam; and means for obtaining spatial distribution information on the intensity of the received light and analyzing this spatial distribution information on the intensity of the received light based on a prescribed determination criterion to determine the state of alignment between the apparatus and the eye.

In the conventional systems, alignment is determined on the basis of one-dimensional alignment information. However, in the above arrangement of this invention, reflected, scattered or disturbing light coming from the direction of the anterior chamber is received to obtain the spatial distribution information on the intensity of light received, which is then analyzed based on predetermined determination criteria to thereby determine the state of alignment between the system and the examinee's eye, thus enabling optimum alignment determination in measuring biological properties by receiving light scattered by biological particles in the anterior chamber scanned by the laser beam.

The above and other features of the present invention will become apparent from the following description made with reference to the drawings.

DETAILED DESCRIPTION OF THE PREFERRED EMBODIMENTS

Figure 1:
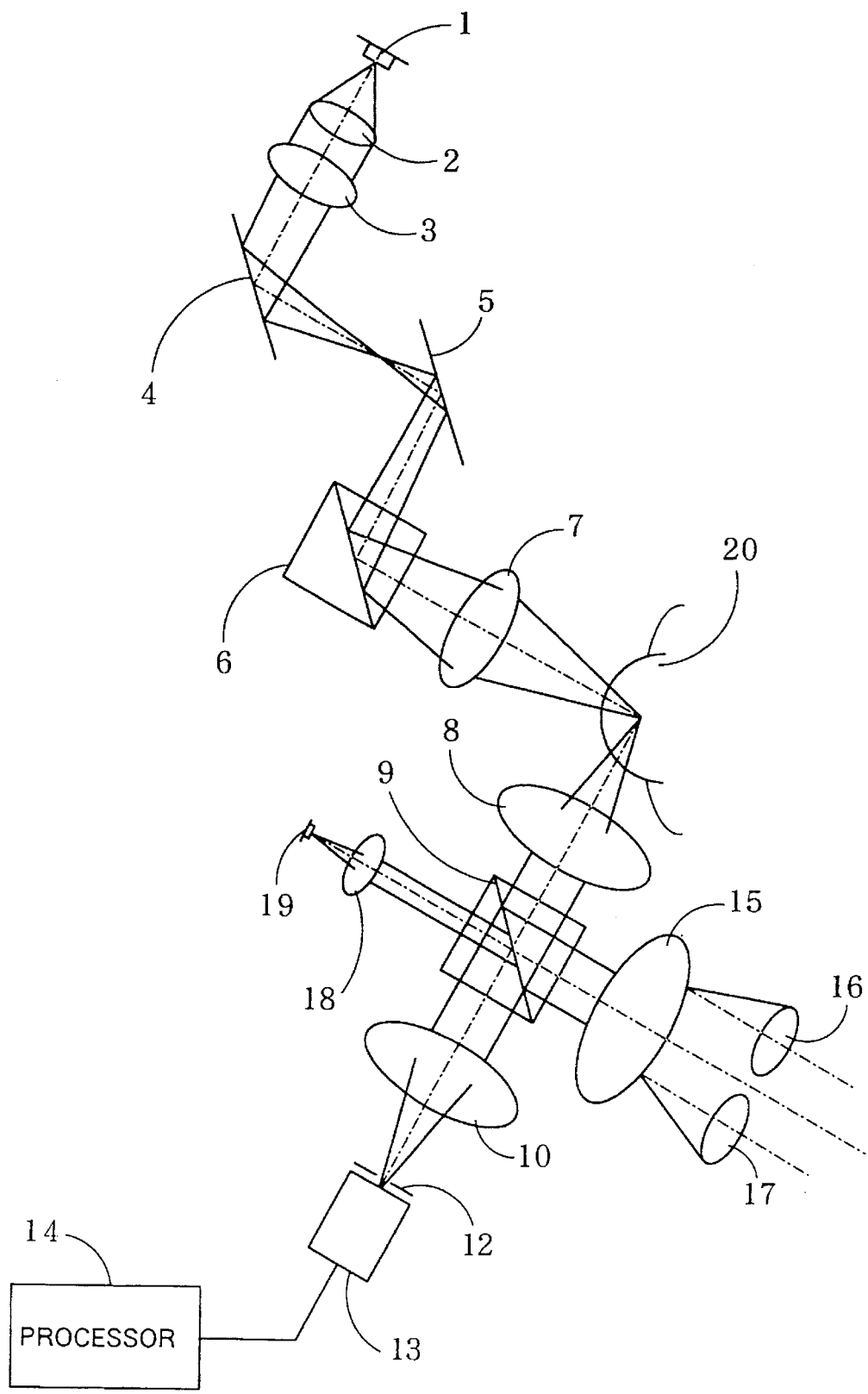
FIG. 1 shows the optical path in an embodiment of an ophthalmic measurement apparatus of the invention.

The measurement system of an apparatus according to the present invention will now be described with reference to FIG. 1. A laser beam from a laser light source 1 is expanded and shaped by lenses 2 and 3 and deflected horizontally by a galvanometer mirror 4 and vertically by a galvanometer mirror 5 while the beam is being focussed into the anterior chamber of an eye 20 by means of a prism 6 and a lens 7. The examiner uses a means such as a joystick (not shown) to control the overall optical system and focus the laser beam on a selected position in the anterior chamber. Light scattered from biological substances such as protein, floating cells and the like in the anterior chamber irradiated by the laser beam is collimated and split into two parts by a semi-reflecting mirror 9. One part of the light beam thus split can be observed by the examiner via lenses 16 and 17. A lens 10 forms the other part of the beam into an image on a mask 12 for limiting the field of vision. Scattered light that passes through the mask 12 is converted into an electrical signal by a photomultiplier 13. The signal is then digitized using the photon count method, and is analyzed by a processor 14. The alignment determination, described below, is done by using the processor 14 to analyze the spatial and time-based distribution of the intensity of the received light. Hereinbelow photon count values will be used to indicate received-light intensity.

A measurement window image produced by an LED or other such light source 19 is formed by a lens 18 at a position that is conjugate with the mask 12, thereby providing the examiner with a measurement window that enables the examiner to establish the positional relationship in the anterior chamber.

The light source 19 can also be used to display the outcome of the state of alignment determination, described below. For example, the state of alignment can be communicated to the examiner by flashing the light source 19 at a frequency corresponding to ranking information, described below, indicating the degree of alignment, or this could be done using lights of different colors, or by using characters. The galvanometer 4 contributes to deflect or scan the laser beam horizontally in the anterior chamber, and the galvanometer 5 scans the laser beam vertically.

Figure 2A:
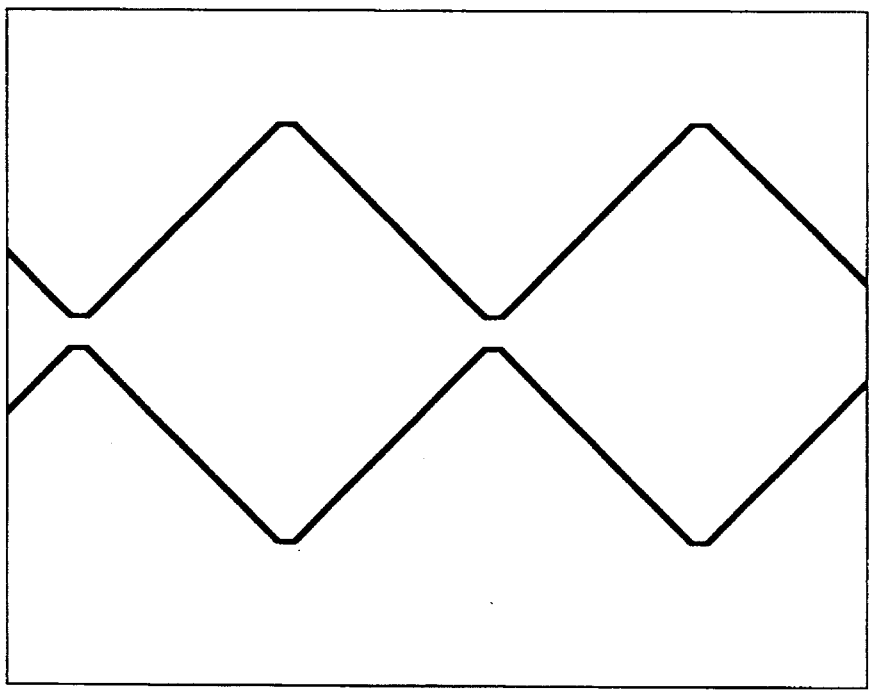
FIGS. 2a and 2b show the waveforms of the signals used to drive the scanning galvanometer mirrors in the invention.
Figure 2B:
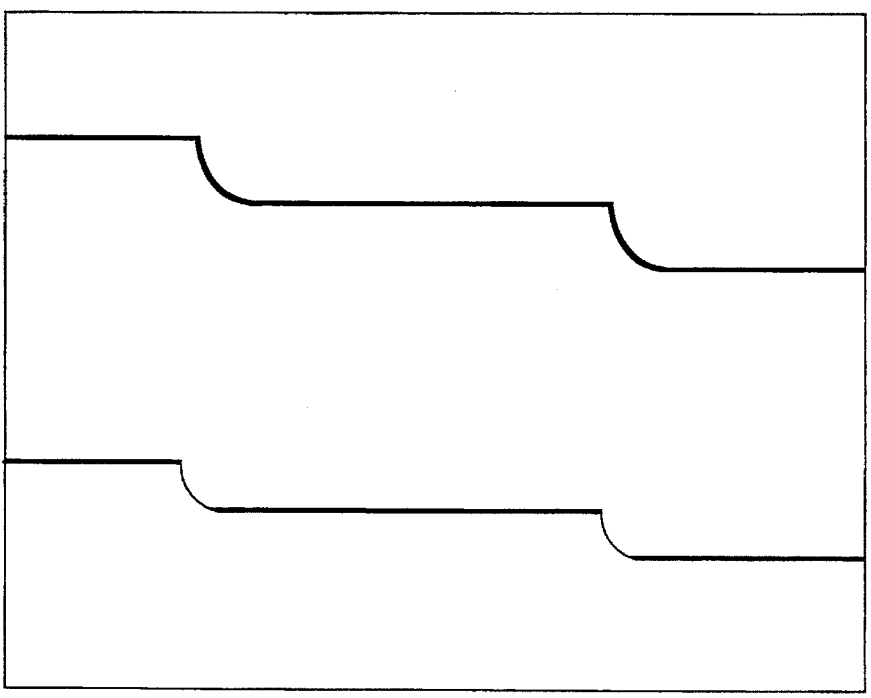

During the measurement process the galvanometer mirrors 4 and 5 are controlled by the signals shown in FIGS. 2a and 2b. As can be seen, horizontal scanning is stopped during measurement by vertical scanning. After the completion of one vertical measurement scan, horizontal scanning is performed during which the position for the laser beam's vertical sweep is set to an initial position.

Figure 3:
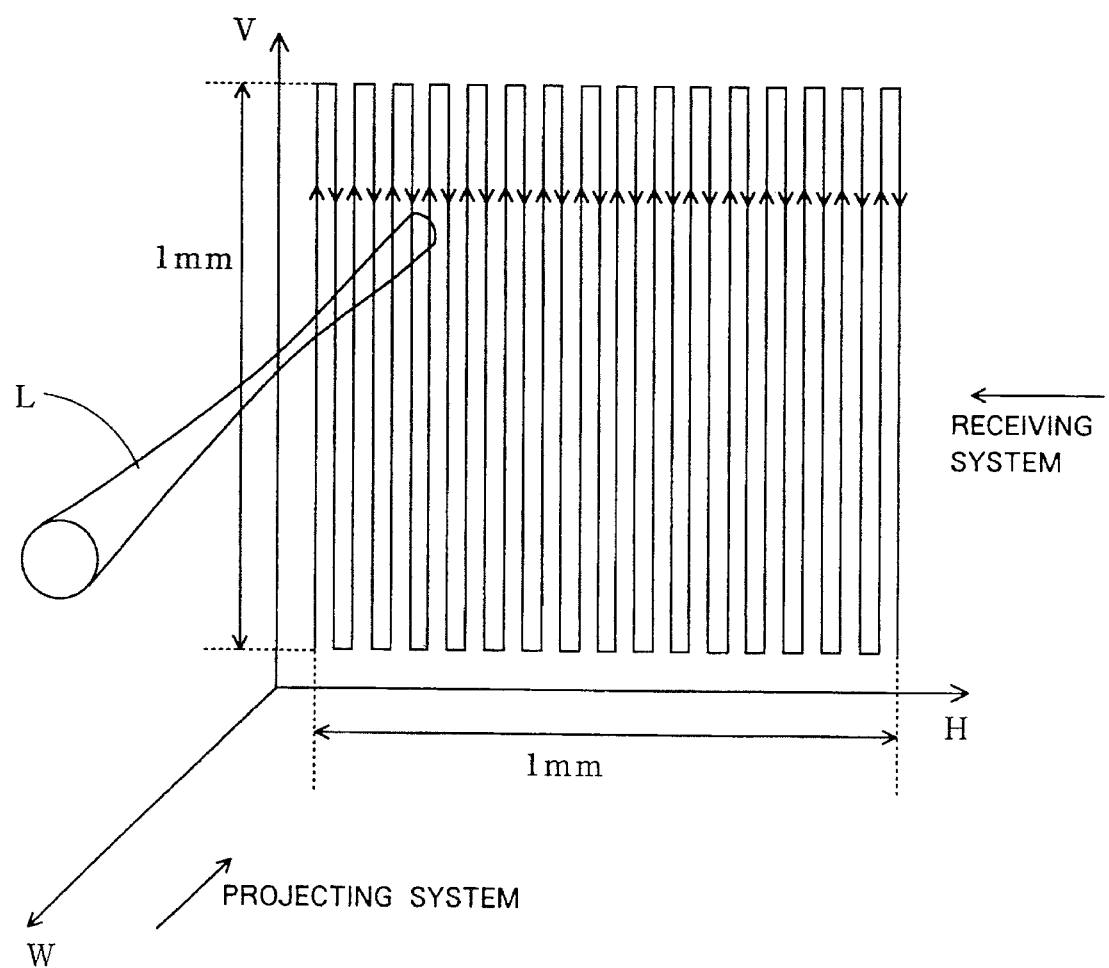
FIG. 3 shows the laser scanning system used during the measurement process.

Laser beam L is swept during measurement as illustrated by FIG. 3, in which "V" denotes the vertical scanning axis and "H" the horizontal scanning axis. In this example the size of the measurement region is 1 mm by 1 mm. When the laser beam is thus swept with the optical system of FIG. 1, assuming that observation is at right-angles to the optical axis and the field of vision in the direction of the optical axis is limited by the mask 12, a three-dimensional measurement region can be defined.

Figure 4:
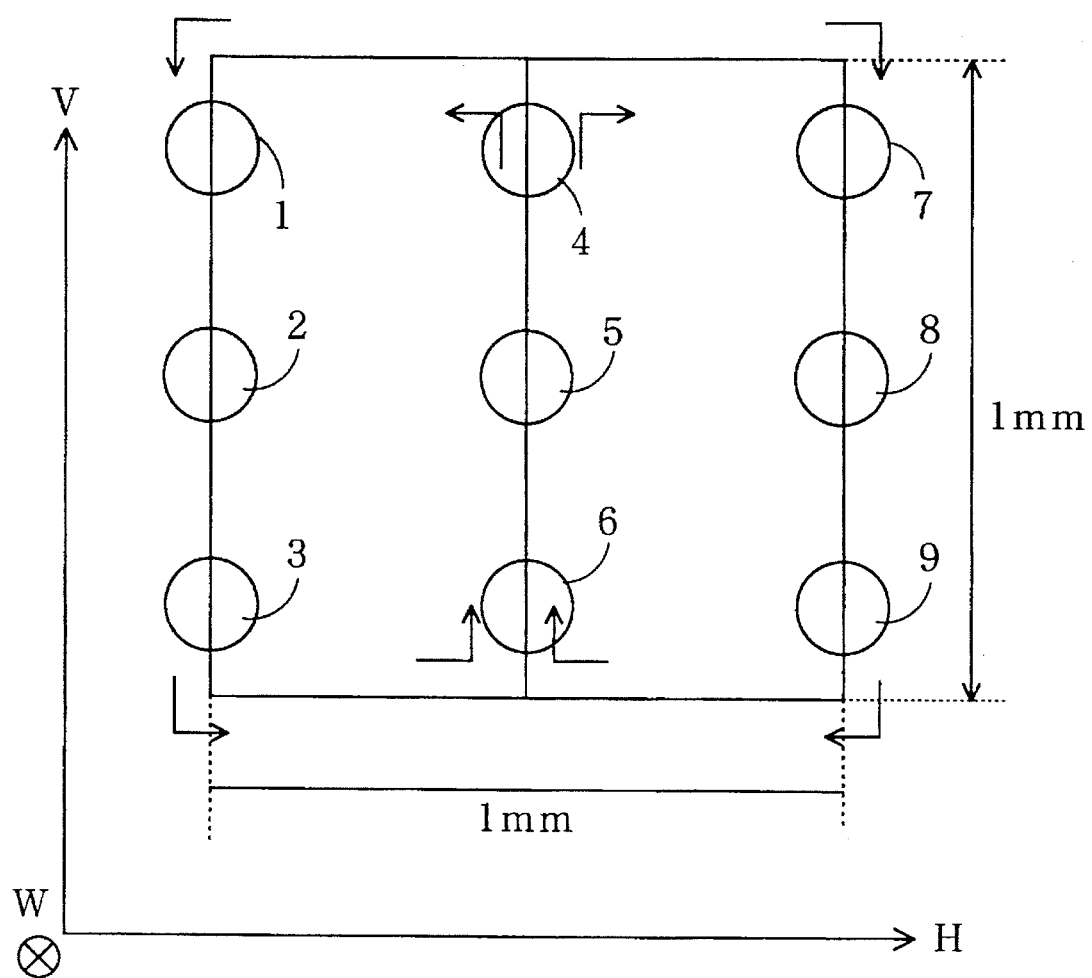
FIG. 4 shows the laser scanning system used during the alignment determination process.

In determining the alignment, the scanning illustrated in FIG. 4 is effected by adjusting the control signal waveforms of FIG. 2. In this example, nine measurement portions, shown as circles 1 to 9, are set within the measurement region. From a comparison of FIGS. 3 and 4, it can be seen that during alignment only measurement scanning lines 1, 16 and 32 are implemented, scanning the center of the measurement region (circle 5) and the peripheral portions (circles 1 to 4 and 6 to 9).

Figure 5A:
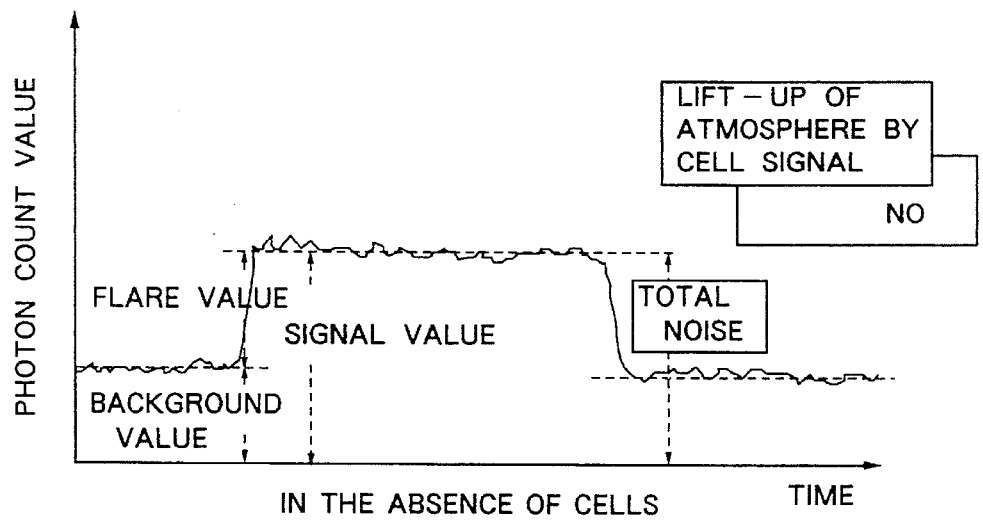
FIGS. 5a and 5b show the intensity of scattered light signals measured by the invention.
Figure 5B:
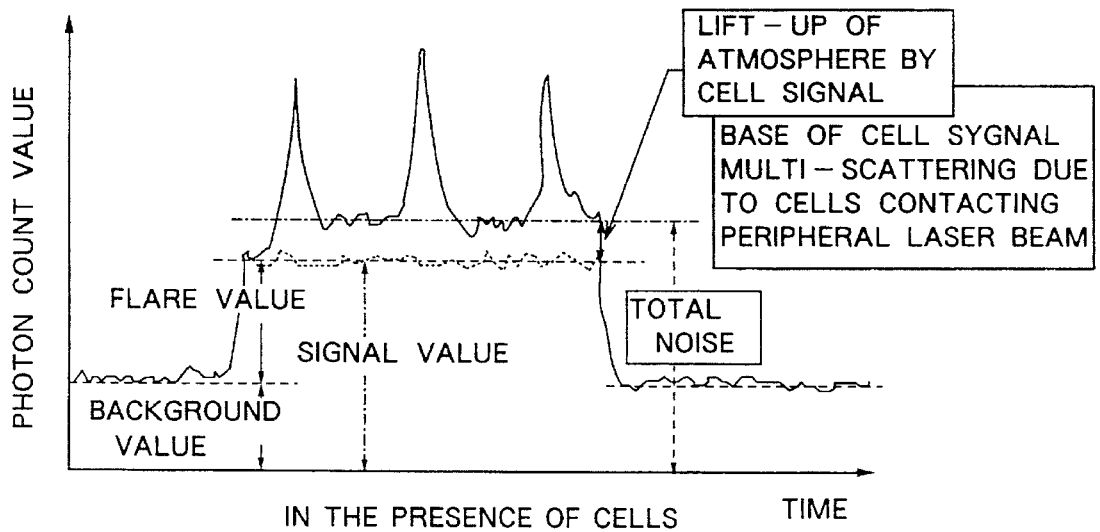
Figure 8:
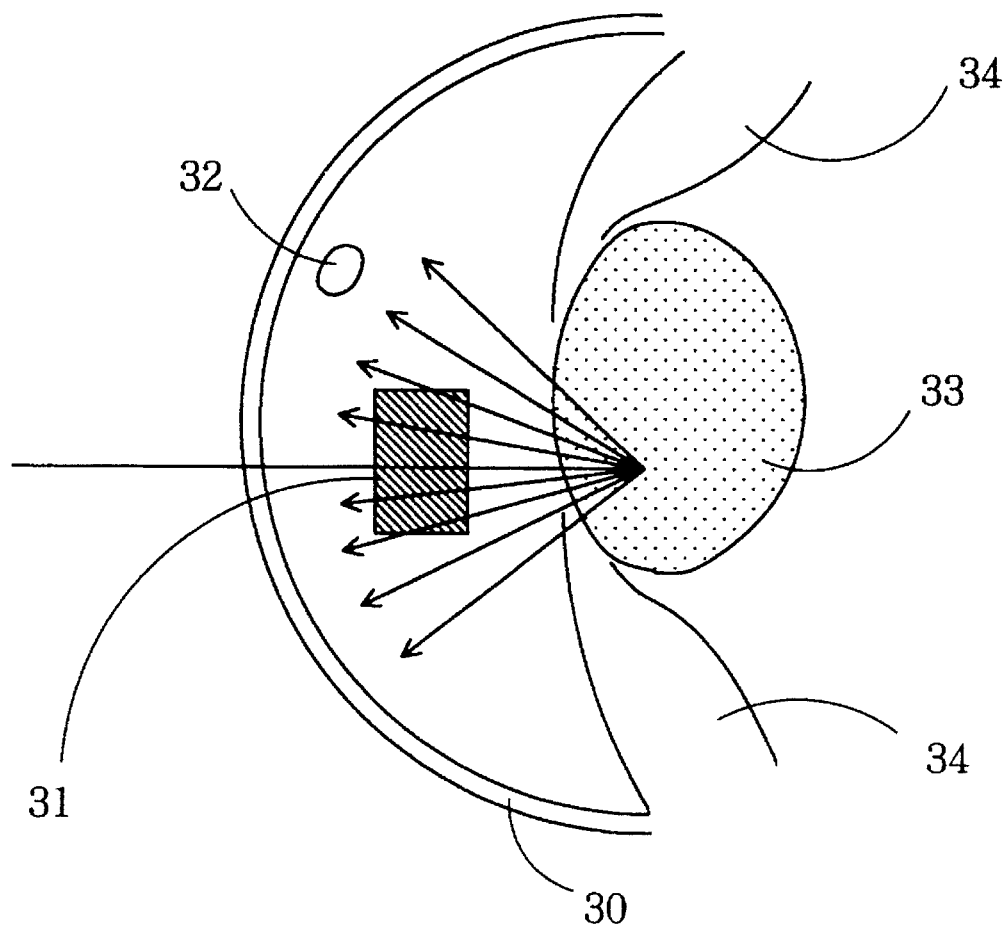
FIG. 8 is a depiction of an eye with a cataract.

With the mode of operation shown by FIG. 3, when using a laser beam to carry out measurement in the anterior chamber of an eye the anterior portion of which is inflamed, light is scattered by protein particles, floating cells and the like in the anterior chamber in FIG. 8. In FIG. 8 reference number 30 indicates the cornea, 31 a measurement window, 32 a spot of light reflected by the cornea 30, 33 the clouded crystalline lens and 34 the iris. When this scattered light is received by the optical system of FIG. 1, time-series data on scattered light intensity, as shown in FIGS. 5a and 5b, can be obtained. Scattered light from floating cells in the anterior chamber, which are much larger in diameter than protein particles such as albumin and globulin (FIG. 5a), show up as spikes (FIG. 5b).

In this way, properties of biological particles can be measured by using a laser beam to scan inside the anterior chamber of an eye and obtaining information on the spatial intensity distribution of the light scattered by the particles. As spatial scanning is used, in order to determine the state of alignment while carrying out such measurements it is necessary to use different determination criteria compared to those used in conventional one-dimensional alignment determination.

To increase the measurement range for improvement in measurement accuracy and to thereby increase the degree of freedom of measurement, for the present invention the following condition were regarded as being the minimum to enable measurement to take place.

Figure 6:
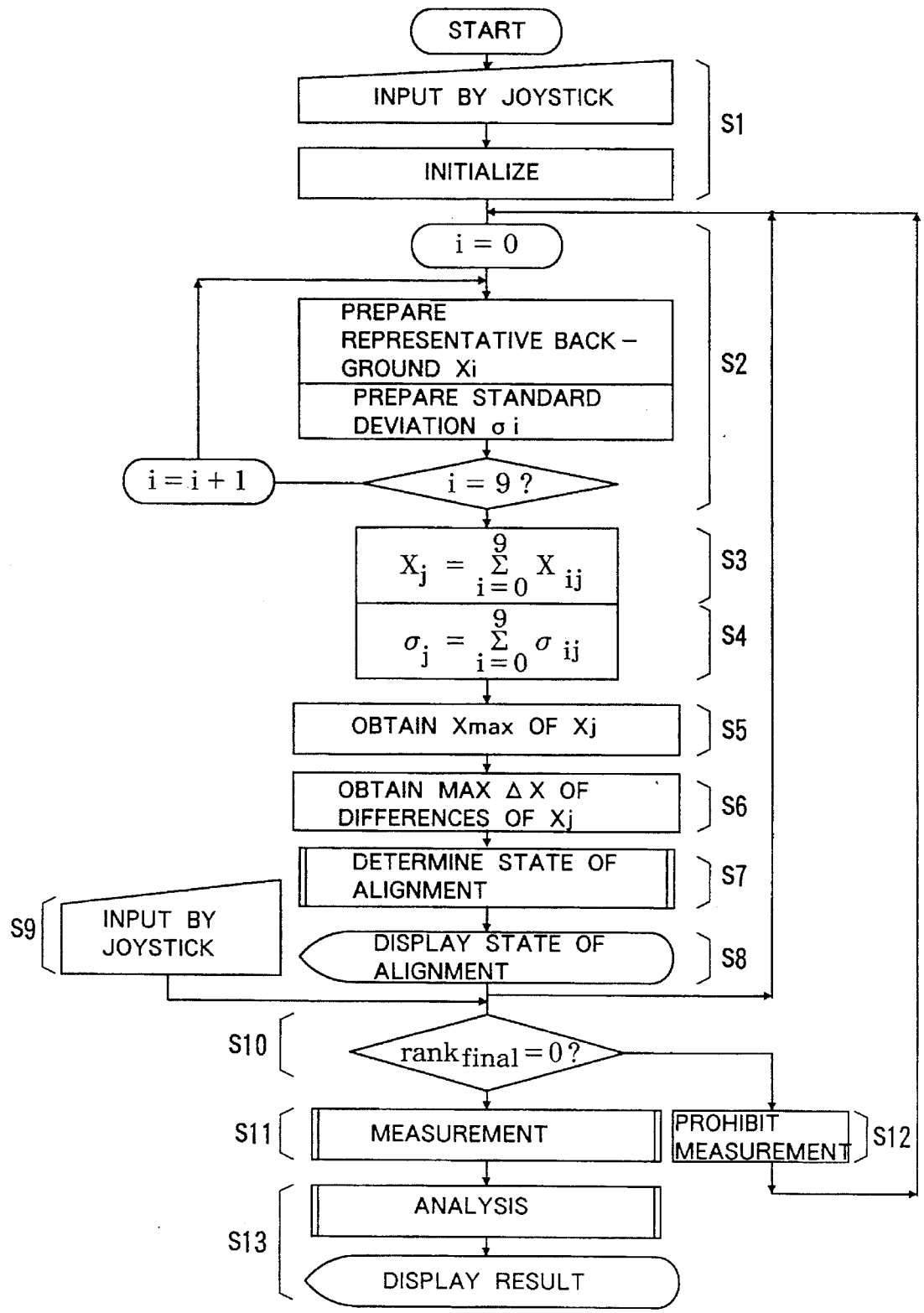
FIG. 6 is a flow chart of the main routine used for the alignment determination process of the invention.
Figure 7:
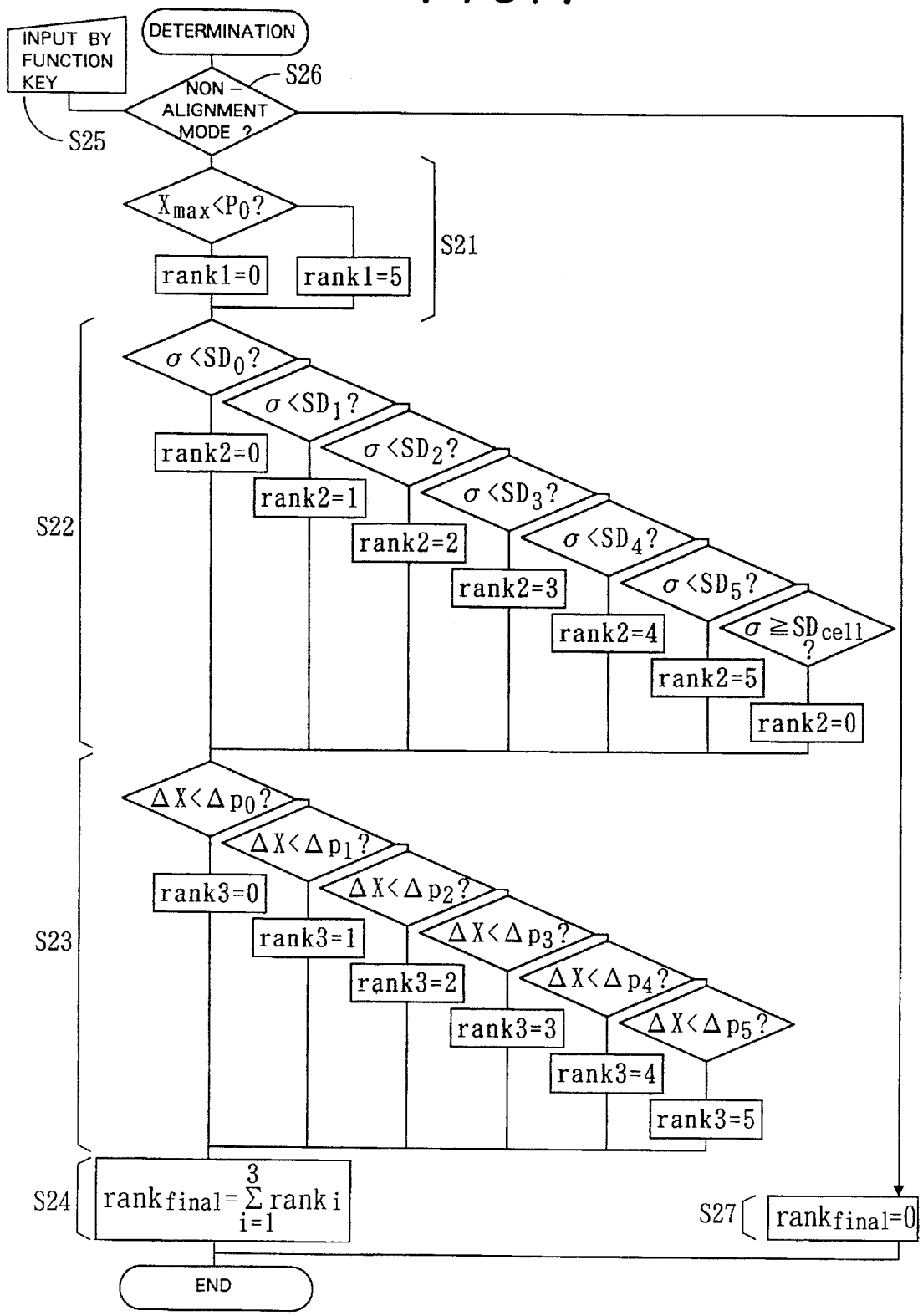
FIG. 7 is a flow chart of the subroutine used for alignment determination.

FIGS. 6 and 7 are flow charts of the alignment determination procedure of the invention. FIG. 6 shows the main routine used during alignment, and FIG. 7 shows the subroutine used to determine the state of the alignment. These flow chart procedures are executed by the processor 14 shown in FIG. 1. The invention will now be described with reference to the flow charts.

The determination of the state of alignment starts in step S1 by the examiner pressing the joystick switch. This initializes the various parameters and devices or elements involved in the alignment determination process. During alignment the laser beam is swept as shown in FIG. 4 by the galvanometer mirrors 4 and 5 under the control of the signals shown in FIG. 2. At this time, when the laser beam reaches the region of the circles 1 to 9 (hereinafter also referred to as "blocks"), the shutter 12 of the photomultiplier 12 opens and time-series measurement starts. For convenience, the blocks are numbered from one to nine as shown in FIG. 4.

Representative background values are extracted from the time-series sampling data obtained from the nine blocks. These representative values are used to determine the degree of the alignment. The ideal procedure is to use the average values of the time-series data to obtain the representative background values. However, calculating the average values takes too much time to enable the determination of the state of alignment to be displayed on a real-time basis. For this reason, the following values are used as representative background values indicating the intensity of the background.

The time-series sampling data obtained from the nine blocks are comprised of (1) background and (2) cell scattered light components. 15 to 20 sampling data are required for one cell signal, so at least sixty time-series sampling data are enough to extract data showing the background of one block concerned.

There are fluctuations in the data, so when there is a low background the time-series sampling data obtained may for example be:

(0, 1, 5, 3, 2, 0, 0, 3, . . . )

Thus, there is a risk that if only the lowest time-series values are used the representative background values will all be zero and will not reflect the actual background state. Therefore, (i) when a certain percentage for example, 40%) or more of the sixty time-series sampling data obtained are zero the representative background value is taken to be zero, and (ii) when less than a certain percentage (for example, 40%) of the sixty time-series sampling data are zero the lowest value, excluding zero, is taken as the representative background value. This method enables representative background values to be established from the time-series data of the blocks, regardless of the intensity of the background and the absence or presence of cells.

Each of the representative background values for the nine blocks is calculated and stored in memory after one data sampling, and this is repeated ten times (step S2). After ten values for each of the nine blocks have thus been accumulated, they are integrated. In step S3 the integral value $$x_j = \sum_{i=0}^{9} x_{ij} (i = 0 \ldots 9)$$

is used to determine the quality of the alignment.

The above xi provides the measurement parameters which can be used to determine the state of alignment. These parameters are xmax, the maximum of xj, and $\Delta x$, the maximum of difference values between the values xj (step S6).

The maximum value $\sigma$ max of the standard deviations in the nine blocks is obtained in step 4. The standard deviation $\sigma j$ in each block j is calculated from the following ten-repeated sum of the standard deviation $\sigma ij$ in the time-series sampling data obtained for each block.

$$\sigma_j = \sum_{i=0}^{9} \sigma_{ij}$$

Using these values, in step S7 the state of alignment is determined in the alignment state determination subroutine. Details of step S7 are shown in FIG. 7.

First, in step S21, in order to exclude cases in which the laser beam impinges on the examinee's eyelashes or the examinee is blinking, an xmax that exceeds the reference photon count is excluded. The photon count that constitutes the reference is set as follows.

It was established through experiments that, using the above measurement method, the photon count produced when the examinee blinks does not exceed a given value (for example, 395 photon counts/msec). The ophthalmic measurement apparatus of this invention has to be able to perform measurements on healthy eyes of any iris color. Also, prior to an IOL insertion operation for cataract, taking into consideration post-operative diagnostic applications, it is also necessary to be able to perform measurements on eyes with cataract. With a cataractous eye, the laser beam impinges on the clouded crystalline lens. This gives rise to the type of reflection/scattering from the crystalline lens 33 shown in FIG. 8. The extent of the effect of such reflected/scattered light will vary depending on the size of the measurement window 31 in the anterior chamber.

When the anterior portion of a cataractous eye was irradiated by laser beam, the light laterally scattered was measured and the photon count per unit sampling time was investigated, it was found that background noise prior to a cataract operation was increased by light received from the clouded crystalline lens. Based on these findings it was judged that the reference photon count used in alignment determination based on the xmax should not exceed 395 photon counts/msec.

Thus, in step S21 the xmax obtained from the nine values xi is compared with the reference value p0 to provide an index rank 1 indicative of a level of the alignment state as follows:

when xmax >p0, rank 1 =5 when xmax $\leq$p0, rank 1 =0.

In step S22 it is checked whether the time-series data of the scattered light intensity measured in the nine blocks are affected by light received or scattered by tissues in the eye.

When measurement is carried out using the optical system of FIG. 1, the time-series data having the scattered light intensity as shown in FIG. 5 are obtained. Scattered light from floating cells in the anterior chamber, which are much larger in diameter than protein particles such as albumin and globulin are observed as spikes of scattered light.

A feature of the photon counting signal is that the standard deviation of signal intensity equals the square root of the average of the signal intensity.

$$\sigma = \sqrt{\text{avg}}$$

here, avg is the average value and $\sigma$ is the standard deviation.

The background consists of light reflected or scattered by the cornea and iris. An examination of the measured time-series data showed that the standard deviation in the case of signals produced by light reflected or scattered by the cornea and iris is higher than the standard deviation of flare scattered light signals.

It therefore follows that when the standard deviation of scattered light intensity markedly differs from the square root of the average, it is possible that some anomalous noise signal is overlaying the signal. A method was therefore adopted in which the values of the standard deviation for the time-series data of each block are compared with the reference values to find what proportion of the overall measured signal was light reflected or scattered by the cornea or iris.

In this respect, an index rank 2 indicative of a level of the alignment state is provided using the above $\sigma$ max and the alignment levels are classified as follows:

0<$\sigma$max$\leq$SD0 rank 2=0

SD0<$\sigma$max$\leq$SD1 rank 2=1

SD1<$\sigma$max$\leq$SD2 rank 2=2

SD2<$\sigma$max$\leq$SD3 rank 2=3

SD3<$\sigma$max$\leq$SD4 rank 2=4

SD4<$\sigma$max$\leq$SD5 rank 2=5

SD5<$\sigma$max$\leq$SDcell rank 2=0

However, when there is a high concentration of floating cells, there is a strong possibility that a cell peak signal will be included among the time-series data of interest. In such a case (for example max is SDcell or above) the rank 2 might be set to a great value. The rank 2 is, however, set to zero in this embodiment. This means that this loop of determination should be skipped.

Step S23 is a check relating to determining the uniformity of the background. The cell recognition can be made even when the background has some gradient. The degree of this gradient is represented as $\Delta xi$, the maximum of the difference values between the representative background values xi of each block. When $\Delta xi$ is 0$\leq\Delta xi \leq\Delta$p0, the uniformity of the background is ensured and cells are correctly recognized. Then an index rank 3 is set to 0 (rank 3=0). The following settings were used for different degrees of $\Delta xi$.

$\Delta$p0$\leq\Delta xi\leq\Delta$p1 rank 3=1

$\Delta$p1$\leq\Delta xi\leq\Delta$p2 rank 3=2

$\Delta$p2$\leq\Delta xi\leq\Delta$p3 rank 3=3

$\Delta$p3$\leq\Delta xi\leq\Delta$p4 rank 3=4

Δp4≦Δxi≦rank 3=5.

In step S24, rank 1, rank 2 and rank 3 obtained in steps S21 to S23 are added to form a "rankfinal" (=rank 1+rank 2+rank 3) indicating the final state of alignment. A rankfinal of zero indicates that the apparatus is in alignment with the eye. Based on the rankfinal value, it is determined whether measurement is possible, and the process reverts from the subroutine of FIG. 7 back to the main routine of FIG. 6. Following this, the light source 19 is operated in accordance with the rankfinal value to thereby communicate the state of alignment to the examiner. During measurement (non-alignment), a rankfinal value of 5 is applied and the process reverts to the main routine.

The state of alignment is indicated by altering the illumination of an index optically projected in the ophthalmoscope. For example the light source 19 can be used to cause the index to flash ON and OFF at a rate corresponding to a rankfinal value, or a light of a certain color can be used (step S8).

The process goes to standby at this point (step S9) until the examiner starts the measurement operation by pressing the push-button of the joystick switch. When the switch has been pressed, measurement can proceed provided that the rankfinal value is zero (steps S10 and s11). If the rankfinal value is not zero, measurement is not allowed to proceed (S10 and S12) and the process for obtaining parameters for determining the state of alignment is repeated. In step S13 the measurement is analyzed and the result is displayed.

Thus, after alignment has been completed the examiner uses the joystick switch to start the measurement process. Even when the system is well aligned, movement or blinking by the examinee during the measurement process may give rise to a background value (that is, a background value acquired during the measurement process) of p0 or above. This results in a determination that something went wrong with the measurement, which is communicated to the examiner in the form of a display in the ophthalmoscope or on a screen. This makes it possible to deal with problems that might arise following the alignment process.

As described above, the measurement can only proceed when the alignment rankfinal value is zero. However, there can be clinical situations in which an eye that is being examined has a high background, and a rankfinal of zero cannot be achieved even when the alignment is geometrically correct. In such cases a state of alignment index of rankfinal ≠0 is maintained. The alignment determination subroutine of FIG. 7 has the following supplemental function to enable reference measurements to be carried out with respect to such examinees.

During alignment, pressing a function key (S25 and S26) forces a rankfinal of zero (S27) regardless of the state of alignment, enabling measurement to take place. However, this can introduce an error factor of 30% or more in the accuracy of the analysis. This fact is displayed to differentiate this from accurate data. This function can only be used for one measurement. Exceeding one measurement causes a reversion to the normal state of alignment determination process under which poor alignment will prevent measurement from taking place.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measurement apparatus comprising:

scanning means for spatially scanning the anterior chamber of an eye with a laser beam;

means for receiving reflected, scattered or disturbing light coming from the anterior chamber scanned by the laser beam; and means for obtaining spatial distribution information on an intensity of the received light and analyzing the spatial distribution information on the intensity of the received light based on a prescribed determination criterion to determine the state of alignment between the apparatus and the eye.

2. An ophthalmic measurement apparatus as set forth in claim 1; wherein the prescribed determination criterion is arranged to ensure a measurable range that is high enough to increase the degree of freedom of measurement and to eliminate a lack of alignment which prevents an accurate measurement from being obtained.

3. An ophthalmic measurement apparatus as set forth in claim 1; wherein the state of alignment is determined by two-dimensionally scanning a target measurement range in the anterior chamber of the eye with the laser beam, receiving light from the anterior chamber at a plurality of measurement points and checking the intensity of received light at the measurement points.

4. An ophthalmic measurement apparatus as set forth in claim 3; wherein a representative background value at each of the measurement points is calculated from the received light at each of the measurement points.

5. An ophthalmic measurement apparatus as set forth in claim 4; wherein a maximum of the representative background values at each of the measurement points is compared with a set value for alignment with the eye.

6. An ophthalmic measurement apparatus as set forth in claim 4; wherein a difference value between the representative background values at the measurement points is compared with a set value for alignment with the eye.

7. An ophthalmic measurement apparatus as set forth in claim 3; wherein a standard deviation of the intensity of the received light at each of the measurement points is compared with a set value to determine whether the received light includes the disturbing light or light scattered or reflected from tissues in the eye, thereby determining the state of alignment.

8. An ophthalmic measurement apparatus as set forth in claim 3; wherein a standard deviation of the intensity of the received light at each of the measurement points is compared with a set value to determine whether the received light includes scattered light signals from floating cells, thereby determining the state of alignment.

9. An ophthalmic measurement apparatus as set forth in claim 8; wherein the standard deviation is not used when the number of signals from the floating cells is such that the signals cannot be separated from background.

10. An ophthalmic measurement apparatus as set forth in claim 2; wherein measurement is prohibited when the determined state of alignment is such that an accurate measurement cannot be obtained.

11. An ophthalmic measurement apparatus as set forth in claim 1; wherein the scanning means scans the anterior chamber of the eye horizontally and vertically.

12. An ophthalmic measurement apparatus comprising:

scanning means for two-dimensionally scanning the anterior chamber of an eye with a laser beam;

means for receiving light coming from the anterior chamber at a plurality of measurement points in a target measurement range defined by the two-dimensionally scanning;

means for calculating a representative background value at each of the measurement points from the received light;

means for comparing the representative background value with a first reference value to provide a first alignment rank level indicative of the state of alignment; and means for determining the state of alignment according to the first alignment rank level.

13. An ophthalmic measurement apparatus as set forth in claim 12, further comprising:

means for calculating a difference value between the representative background values at the measurement points;

means for comparing the difference value with a second reference value to provide a second alignment rank level indicative of the state of alignment; and means for determining the state of alignment according to the first and second alignment rank levels.

14. An ophthalmic measurement apparatus as set forth in claim 13; further comprising:

means for calculating a standard deviation of intensities of the received light at each of the measurement points;

means for comparing the standard deviation with a third reference value to provide a third alignment rank level indicative of the state of alignment; and means for determining the state of alignment according to the first and third alignment rank levels.

15. An ophthalmic measurement apparatus as set forth in claim 14; wherein a maximum of the standard deviations at the measurement points is compared with the third reference value.

16. An ophthalmic measurement apparatus as set forth in claim 11; wherein a maximum of the difference values between the representative background values at the measurement points is compared with the second reference value.

17. An ophthalmic measurement apparatus as set forth in claim 12; wherein a maximum of the representative background values at the measurement points is compared with the first reference value.

18. An ophthalmic measurement apparatus as set forth in claim 12; wherein the alignment rank level is displayed and communicated to the examiner.

19. An ophthalmic measurement apparatus as set forth in claim 12; further comprising means for selecting whether or not to perform or communicate the state of alignment.

20. An ophthalmic measurement apparatus comprising:

means for two-dimensional scanning the anterior chamber of an eye with a laser beam;

means for receiving light coming from the anterior chamber at a plurality of measurement points in a target measurement range defined by the two-dimensional scanning;

means for calculating a representative background value at each of the measurement points from the received light;

means for calculating a difference value between the representative background values at the measurement points;

means for comparing the difference value with a reference value to provide an alignment rank level indicative of the state of alignment; and means for determining the state of alignment according to the alignment rank level.

21. An ophthalmic measurement apparatus as set forth in claim 20; wherein a maximum of the difference values between the representative background values at the measurement points is compared with the reference value.

22. An ophthalmic measurement apparatus comprising:

means for two-dimensionally scanning the anterior chamber of an eye with a laser beam;

means for receiving light coming from the anterior chamber at a plurality of measurement points in a target measurement range defined by the two-dimensional scanning;

means for calculating a standard deviation of intensities of received light at each of the measurement points;

means for comparing the standard deviation with a reference value to provide an alignment rank level indicative of the state of alignment; and means for determining the state of alignment according to the alignment rank level.

23. An ophthalmic measurement apparatus as set forth in claim 22; wherein a maximum of the standard deviations at the measurement points is compared with the reference value.

24. An ophthalmic measurement apparatus comprising:

first scanning means for scanning a measurement region of an eye horizontally with a beam of light;

second scanning means for scanning the measurement region of the eye vertically with the beam of light;

light receiving means for receiving light from the measurement region of the eye scanned by the beam of light; and calculating means for calculating spatial distribution information on an intensity of the received light and analyzing the spatial distribution information based on a prescribed determination criterion to determine the state of alignment between the ophthalmic measurement apparatus and the eye.

25. An ophthalmic measurement apparatus as set forth in claim 24; wherein the prescribed determination criterion is arranged to ensure a measurable range that is high enough to increase the degree of freedom of measurement, and to eliminate a lack of alignment which prevents an accurate measurement from being obtained.

26. An ophthalmic measurement apparatus as set forth in claim 25; wherein measurement is prohibited when the determined state of alignment is such that an accurate measurement cannot be obtained.

27. An ophthalmic measurement apparatus as claimed in claim 24; wherein the first and second scanning means scan a target measurement range in the measurement region, the light receiving means receives light from the measurement region at a plurality of measurement points, and the calculating means checks the intensity of received light at the measurement points to thereby determine the state of alignment.

28. An ophthalmic measurement apparatus as set forth in claim 27; wherein a representative background value at each of the measurement points is calculated from the received light at each of the measurement points.

29. An ophthalmic measurement apparatus as set forth in claim 28; wherein a maximum of the representative background values at each of the measurement points is compared with a set value for alignment with the eye.

30. An ophthalmic measurement apparatus as set forth in claim 28; wherein a difference value between the representative background values at the measurement points is compared with a set value for alignment with the eye.

31. An ophthalmic measurement apparatus as set forth in claim 27; wherein a standard deviation of the intensity of the received light at each of the measurement points is compared with a set value to determine whether the received light includes the disturbing light or light scattered or reflected from tissues in the eye, thereby determining the state of alignment.

32. An ophthalmic measurement apparatus as set forth in claim 27; wherein a standard deviation of the intensity of the received light at each of the measurement points is compared with a set value to determine whether the received light includes scattered light signals from floating cells, thereby determining the state of alignment.

33. An ophthalmic measurement apparatus as set forth in claim 32; wherein the standard deviation is not used when the number of signals from the floating cells is such that the signals cannot be separated from background.

* * * * *